US005663155A

United States Patent [19]
McCaffrey et al.

[11] Patent Number: 5,663,155
[45] Date of Patent: Sep. 2, 1997

[54] COMPOSITIONS FOR THE TREATMENT OF PARASITIC INFECTIONS

[75] Inventors: Ronald P. McCaffrey, Needham, Mass.; Hans L. R. Wigzell, Hagersten, Sweden

[73] Assignee: The University Hospital, Boston, Mass.

[21] Appl. No.: 351,068

[22] Filed: Nov. 30, 1994

[51] Int. Cl.$^6$ .......................... A61K 31/70; C07H 19/16
[52] U.S. Cl. .................... 514/45; 514/46; 536/27.21; 536/27.6; 536/27.61; 536/27.62; 536/27.63; 536/27.7; 536/27.8; 536/27.81
[58] Field of Search ................ 514/45, 46; 536/27.6, 536/27.61, 27.62, 27.63, 27.7, 27.8, 27.81, 27.21

[56] References Cited

U.S. PATENT DOCUMENTS

| | | | |
|---|---|---|---|
| 4,997,818 | 3/1991 | McCaffrey et al. | 514/45 |
| 5,180,714 | 1/1993 | Sufrin et al. | 514/46 |
| 5,292,725 | 3/1994 | Frendergast | 514/46 |

FOREIGN PATENT DOCUMENTS 0450102  10/1990  European Pat. Off. .

OTHER PUBLICATIONS

Abstract—"Cordycepin Activates An Apoptotic Cascade in TdT–Positive Leukemia Cells," McCaffrey, The American Society of Hematology, 35th Annual Meeting, Dec. 3–7, 1993.
Abstract—"Cordycepin Is Selectively Cytotoxic For TdT–Positive Cells," Yener Koc, The American Society of Hematology, 35th Annual Meeting, 1992.
Abstract—"Cordycepin Selectively Kills TdT–Positive Cells," Yener Koc, The American Society of Hematology, 35th Annual Meeting, 1993.
Abstract—"Induction of Apoptosis In TdT Leukemia/Lymphoma Cells By Cordycepin (3'–dA)," Yener Koc, ASCO Annual Meeting, May 14–17, 1994.
"Adenosine Analogues As Antimetabolites Against *Plasmodium Falciparum*Malaria," Coomber, et al., *International Journal of Parasitology*, vol. 24, No. 3, pp. 376–365, 1994.
"Adenosine Deaminase From Human Erythrocytes: Purification and Effects of Adenosine Analogs," Agarwal, et al., *Biochemical Pharmacology*, vol. 24, pp. 693–701, 1975.
"Antimalarial Action of Nitorbenzylthioinosine in Combination with Purine Nucleoside Antimetabolites," Gero, et al., *Moloecular and Biochemical Parasitology*, vol. 34, pp. 87–98, 1989.
"Biochemistry of Plasmodium (Malarial Parasites)," Sherman, *Microbiological Reviews*, vol. 43, No. 4, pp. 453–495, Dec. 1979.
"Characterization of Adenosine Deaminase From the Malarial Parasite, *Plasmodium Lophurae*, and Its Host Cell, The Duckling Erythrocyte", Schimandle, et al., *Biochemical Pharmacology*, pp. 115–121, 1983.

"Enzymes of Purine and Pyrimidine metabolism From the Human Malaria Parasite, *Plasmodium Falciparum*," Reyes, et al., *Molecular and Biochemical Parasitology*, vol. 5, pp. 275–290, 1982.
"Human Melanoma Cells Sensitive To Deoxyadenosine and Deoxyinosine," Parsons, et al., *Biochemical Pharmacology*, vol. 35, No. 4, pp. 655–660, 1986.
"Human Malaria Parasite Adenosine Deaminase, Characterization in Host Enzyme–Deficient Erythrocyte Culture," Daddona, et al., *The Journal of Biological Chemistry*, vol. 259, No. 3, pp. 1472–1475, Feb. 10, 1984.
"Incorporation of 2–Halogeno–2'–Deoxyadenosine 5–Triphosphates into DNA During Replication by Human Polymerases αand β," Hentosh, et al., *The Journal of Biological Chemistry*, vol. 265, No. 7, pp. 4033–4040, Mar. 5, 1990.
"In Vitro Susceptibilities of *Plasmodium Falciparum* to Compounds Which Inhibit Nucleotide Metabolism," Queen, et al., *Antimicrobial Agents and Chemotheraphy*, vol. 34, No. 7, pp. 1393–1398, Jul. 1990.
"Metabolism of Adenosine Analogues By *Schistosoma Mansoni* and the Effect of Nuceloside Transport Inhibitors," Kouni, et al., *Biochemical Pharmacology*, vol. 36, No. 7, pp. 1099–1106, 1987.
"On the mechanism of feedback Inhibition of Purine Biosynthesis de Novo in Ehrlich Ascites Tumor Cells in Vitro," Henderson, et al., *The Journal of Biological Chemistry*, vol. 240, No. 7, Jul. 1965.
"Purine and Pyrimidine Metabolism in the Trypanosomatidae," Hammond, et al., *Molecular and Biochemical Parasitiology*, vol. 13, pp. 243–261, 1984.
"Purine Nucleoside Phosphorylase of the Malarial Parasite, *Plasmodium Lophurae*, " Schimandle, et al., *The Journal of Biological Chemistry*, vol. 260, No. 7, pp. 4455–4460, Apr. 10, 1985.
"Purines and Pyrimidines in Malarial Parasites," Gero, et al., *Blood Cells*, vol. 16, pp. 467–484, 1990.
"Purine Salvage and Metabolism in *Babesia Bovis*," Matias, et al., *Parasitol Res.*, vol. 76, pp. 207–213, Feb. 1990.

(List continued on next page.)

Primary Examiner—James O. Wilson
Attorney, Agent, or Firm—James Remenick; Baker & Botts, L.L.P.

[57] ABSTRACT

The invention relates to compositions comprising an adenosine derivative and a deaminase inhibitor for the prevention and treatment of parasitic infections by eukaryotic organisms. Parasitic infections which are treatable and preventable with these compositions include malaria, trypanosomiasis, leishmania, toxoplasmosis, sarcocystis, pneumocystis, schistosomiasis, blood flukes and elephantiasis. The invention also relates to methods for utilizing these compositions in treatment regiments. Treatments may be either in vivo or in vitro. In vivo treatments involve administration of compositions of the invention to mammals suspected or at risk of being infected with a parasitic organism. In vitro treatments involve incubation of cells, tissues, biological products derived from living materials or foods with compositions of the invention to inhibit or prevent further infection.

50 Claims, No Drawings

OTHER PUBLICATIONS

"Pryimidine Analogues," Hochster, et al., *Metabolic Inhibitors, A Comprehensive Treatise,* vol. 1, pp. 239–285, 1963.

"Quantitative Assessment of Antimalarial Activity In Vitro by a Semiautomated Microdilution Technique," Desjardins, et al., *Antimicrobial Agents and Chemotheraphy,* vol. 16, No. 6, pp. 710–718, Dec. 1979.

"Selective Toxicity of Deoxyadenosine Analogues In Human Melanoma Cell Lines," Parsons, et al, *Biochemical Pharmacology,* vol. 35, No. 22, pp. 4025–4029, Nov. 15, 1986.

"Stage–Specific alteration of Nucleoside Membrane Permeability and Nitrobenzylthioinosine Insensitivity in *Plasmodium Falciparum* Infected Erythrocytes," Gero, et al., *Molecular and Biochemical Parasitology,* vol. 27, pp. 159–170, Jan. 1988.

"Synchronization of *Plasmodium Falciparum* Erythrocytic Stages in Culture," Lambros, et al., *J. Parasitol,* vol. 65, No. 3, pp. 418–420, 1979.

"The Toxicity of Adenosine Analogues Against *Babesia Bovis* In Vitro," *Journal for Parasitology,* vol. 21, No. 6, pp. 747–751, 1991.

Abstract—Johns, et al., "Enhancement of the Biological Activity of Cordycepin (3'Deoxyadenosine) by the Adenosine Deaminase Inhibitor 2'–Deoxycoformycin", Biochem. Pharmacol., vol. 25, No. 12, Oct. 11, 1976.

Abstract—Adamson, et al. "Enhancement of the Biological Activity of Adenosine Analogs by the Adenosine Deaminase Inhibitor 2'–Deoxycoformycin",Pharmocology, vol. 15, No. 1, May 9, 1977.

Abstract—Yamasa Shoyu KK "Cordycepin and (2')–deoxycoformicin prepd, simultaneously by culturing a strain of Aspergillus or Emericella" JP,A,52 130 991, Nov. 2, 1977.

Moorman et al., "Antiprotozoal Activity of 3'–Deoxinosine," Biochemical Pharmacology, vol. 42, No. 2, pp. 207–212, (1991).

COMPOSITIONS FOR THE TREATMENT OF PARASITIC INFECTIONS

RIGHTS IN THE INVENTION

This invention was made with United States Government support under grant number CA 52020, awarded by the national Cancer Institute of the National Institutes of Health, and the United States Government has certain rights in the invention.

BACKGROUND OF THE INVENTION

1. Field of the Invention

This invention relates to compositions useful for the prevention and treatment of parasitic infections which cause diseases such as malaria, trypanosomiasis, leishmania, schistosomiasis and elephantitis. Useful compositions contain an adenosine or adenosine derivative and, optionally, a deaminase inhibitor. Compositions may be used in vivo to treat patients and also in vitro to inactivate or destroy infectious organisms in cultured cells, in fluids such as blood and blood products, in biological products derived from cells and in foods. This invention also relates to methods for treating or preventing parasitic infections with these compositions.

2. Description of the Background

Parasitism is a normal and ubiquitous part of all aspects of life and has been found to occur in nearly every living organism. A wide variety of organisms parasitize prokaryotics and an even wider variety plants and animals. As a general rule, the more complex the host the greater the number and variety of parasites which are possible and probable.

There is a diverse array of host-parasite relationships found to occur between parasites and hosts. These relationships can be divided into three major groups, mutualism, commensalism and true parasitism. Mutualism, or mutual symbiosis, occurs in those relationships where both the parasite and the host receive some benefit. One example of this type of relationship is found between the protozoan that inhabits the termite gut and the termite. Termites ingest wood and play an important if not essential role in the life cycle of a forest. Termites can perform this task because of the particular flora which inhabit their gut. These microorganisms carry and express the enzymes necessary to break down cellulosic materials, but do not appear to be detrimental to the termite. The benefits to both host and parasite are clear. Another form of parasitism is commensalism where one member of the association receives all or at least most of the benefits of the relationship while the other is neither harmed or benefited. True parasitism is where the parasite inflicts some degree of injury or damage to the host. When the damage becomes pathogenic, intervention is required to save or minimize damage to the host.

In theory, diseases and disorders that should be most easily treated are those caused by organisms which are distinguishable from the host, precisely the situation found in parasitism. It should be possible to selectively kill or render the infecting organism nonpathogenic without destroying the host by taking advantage of a fundamental difference between the host and the parasite. Unfortunately, this is all too often not possible or unsuccessful because of an inability of the available drugs to destroy the organism at a concentration which is non-toxic to the host. This is especially true with regard to eukaryotic parasites.

Eukaryotic organisms which may be parasitic are varied and diverse. Some, such as *Dracunculus medinensis*, are over a meter in length whereas others, for example viruses, are microscopic. One of the largest groups of parasites are those which infect the gastrointestinal system. These include organisms which inhabit the mouth, stomach, small and large intestines, the upper respiratory passages and the urogenital tract. The list includes species of the genera Entamoeba such as *Entamoeba histolytica*, *E. coli* and *E. poleki*, flagellates such as *Giardia lamblia*, *Dientamoeba fragilis* and *Trichomonas vaginalis*, sporozoans such as *Isospora belli* and *Toxoplasma gondii*, sarcocysts and the ciliate *Balantidium coli*. It also comprises a number of commensals, species of questionable pathogenicity and certain opportunistic pathogens and commensals. These organisms have a world-wide distribution pattern with a prevalence that varies roughly with the measure of sanitation available in the area. Their degree of pathogenicity varies greatly both within and between the various genera and species.

Amebiasis has been implicated in dysenteric diseases, non-dysenteric colitis, acute non-suppurative hepatitis and liver and pulmonary abscesses. Treatments vary with the stage of the infection. The mainstays include iodohydroxyquinoline, diiodohydroxyquin (Diodoquin) and tetracycline. Additional compounds which have demonstrated utility include metronidazole (Flagyl) and diloxanide furoate (Furamide). Although most antibiotics are ineffective, intravenous amphotericin B, oral rifampin and certain combinations which appear to act synergistically may be used. Flagellates are treated with quinacrine hydrochloride, an acridine dye, or metronidazole (Flagyl). Ciliates such as *Balantidium coli* are treated with oxytetracycline (Terramycin) or diiodohydroxyquin (Diodoquin).

Another group of parasites that infects the gastrointestinal tract are the intestinal nematodes which is believed to encompass over 500,000 different species. These are the most worm-like of the parasitic animals with generally cylindrical shapes, tapered at both ends, and covered with a tough protective layer or cuticle. They have a complete digestive tract with both oral and anal openings on the separate sexes. Some nematodes are obligate parasites such as Wuchereria while others have a free-living period. Most are not long-lived and to persist in a host, must be continually reinfected.

The major intestinal round worm is *Ascaris lumbricoides* which ranges in size from 20 cm to 35 cm and is estimated to infect over 650 million people in the world today. Most of these infections are asymptomatic, but large numbers of parasite bodies can cause serious gastrointestinal disorders in heavy infestations. These worms can migrate to various organs and cavities within the body. The degree of pathogenic severity depends to a large extent on the area affected.

The pinworm, *Enterobius vermicularis*, is the most common helminth parasite on the temperate regions of the world. Spread is facilitated in crowded and unsanitary conditions. This organism is generally considered to be a commensal parasite. Symptoms range from mild irritation to sever inflammation, especially in those individuals who may be hypersensitivity to its secretions.

The hookworm occurs in both new and old world varieties. The new world hookworm, *Necator americanus* is found over the Western hemisphere and is still prevalent in certain areas of the United States. The old world hookworm, *Ancylostoma duodenale*, is found mainly in Europe and the Mediterranean and both varieties are prevalent in South America. Although most symptoms are fairly mild, such as itching and allergic reactions, there is a direct correlation between worm load and anemia. These parasites consume a substantial portion of the available iron from infected individuals and for those whose nutrition is already subadequate, severe complications including mental and physical retardation can result.

Other nematodes include *Ancylostoma braziliense* and *A. caninum*, the causative agents of cutaneous larva migrans, *A. philippine* the causative agent of philippine capillariasis which has a fairly high fatality rate, *Strongyloides stercoralis* which produces local lesions by penetrating the skin of human hosts, and the whipworm, *Trichuris trichiura* which has a worldwide distribution and a symptomology that directly correlates to infectious load. Some of the more problematic nematodes include those acquired from fish. This includes the roundworm larvae belonging to the genera Anisakis and Phocanema, and also related genera. Infections are reported from ingestion of raw, undercooked or even inadequately pickled fish. Diseases in humans are accompanied by a low grade eosinophilia and occult blood, but are generally not life threatening.

The most effective treatment presently available against the intestinal nematodes may be pyrantel pamoate (Antiminth) which has a cure rate of over 95% for ascaris (V. M. Villarejos et al., Am. J. Trop. Med. Hyg. 20:842–45, 1971). Other drugs which have proved to be useful include thiabendazole (Mintezol), pyrvinium pamoate, bephenium (Alcopara), mebendazole (Vermox), and combinations of these compounds administered either simultaneously or in a multi-course treatment regiment The blood and tissue dwelling nematodes include the filariae which are long, thread-like nematodes that infect and reside in the blood and lymphatic systems, and also tissues such as the subcutaneous and deep connective tissues. These include *Brugia malayi*, *B. timori*, *Loa loa* (the African eye worm), *Dipetalonema stretocerca* and *Onchocerca volvulus*. Bancroftian filaria are widely distributed throughout the tropics and subtropics. One characteristic representative of this group is the parasite *Wuchereria bancrofti* which is transmitted by mosquitoes. Within the infected mosquito, microfilaria undergo an essential developmental cycle transforming into infective larva. These larvae then enter the proboscis of the mosquito and, at the mosquito's next blood meal, leave the proboscis and enter the host through the puncture hole left by the mosquito. Clinical manifestations vary and appear to depend upon the numbers of infecting organisms and the present physical state of the host. Early symptoms of filariasis are fever, lymphangitis and lymphadenitis. Attacks are sometimes referred to as elephantoid fever with an associated lymphangitis most commonly affected the lymph nodes. Elephantiasis, the enlargement of one or more limbs, scrotum, breasts or vulva, is relatively uncommon and a late complication of filariasis. It is caused by obstruction of lymph flow and typically accompanied with multiple abscesses on the body. Obstruction is not, as is often believed, caused by massive numbers of living or dead filariae occluding vessels, but is more likely caused by an allergic reaction to the filaria in the tissues which surrounds the vessels. Individuals with especially severe infectious loads have multiple complications.

Treatment is usually an antihistaminic such as promethazine hydrochloride co-administered with steroids to reduce inflammation. The standard filaricide is diethylcarbamazine and its derivatives which is often followed with a regiment of suramin. These treatments often require months of administration, a significant problem in most ares of the world.

Another common tissue dwelling nematode is *Trichinella spiralis*. In intestinal infections, the worm is found in the gut mucosa and usually asymptomatic. Upon entry into a migratory phase, these parasites travel through the body lodging in muscles forming encased larval cysts that can produce severe symptoms. Muscle cysts can cause hemorrhages, edema, visual disturbances and pain. Central nervous system involvement is common in more advanced stages and can lead to death.

Treatment of symptomatic infections usually involves corticosteroids such as prednisone or prednisone derivatives. Thiabendazole may be somewhat effective, but its utility has not been proven. Mebendazole is somewhat effective in preventing tissue infection and may also be useful against the tissue phase as well.

Tissue coccidia are intestinal parasites of man with a more cosmopolitan distribution. *Toxoplasma gondii* infects a variety of vertebrates including cats which can transfer the disease to man. Most infections are benign, however, infections of cardiac patients and infections during pregnancy can lead to serious complications. The only treatment available is long term administration of pyrimethamine with supplements of folic add to counter expected suppression of bone marrow cell proliferation.

Sarcocystis, babesia and pneumocystis, three additional forms of tissue coccidia, are intestinal parasites of man and domesticated and wild animals. Infants and young children are especially sensitive to these diseases. Treatment usually involves combinations of sulfadiazine, pyrimethamine and leucovorin, or sulfamethoxazole and famethoxazole. Side effects, some of which can be severe, are common.

Another tissue parasite, common in the areas from Asia to the Arabian peninsula and from Africa to southern Russia is *Dracunculus medinensis*, the guinea worm. These worms develop in water as copepods and are ingested or infected through the skin. They live and mature in the deep connective tissues of the body for approximately one year. Mature worms migrate to a position close to the skin forming ulcerations. Upon contact with water, the female worms discharge large numbers of copepods into the water to repeat the cycle. Worms generally must be removed surgically which is an extremely difficult procedure due to the fragility of the worm's body which if ruptured floods the patient's body with toxins and extremely allergenic substances. Secondary infections are common and represent just one of the more persistent problems associated with this infection. Treatment typically involves oral administration of niridazole (Ambilhar) or metronidazole. These compounds tend to produce tolerable side effects including nausea, vomiting and diarrhea, and also more severe effects such as anemia, paresthesia and electrocardiographic changes.

Among the most important of the blood and tissue dwelling protozoa are the hemoflagellates. The principle families of this group are the Trypanosomidae and Leishmania, both of which are a significant source of morbidity and mortality in the world today.

Trypanosomiasis occurs in many different forms in man. African sleeping sickness, caused by *Trypanosoma brucei gambiense*, the more virulent *T. brucei rhodesiense*, and *T. brucei brucei* which is restricted to animal hosts, are nearly impossible to distinguish morphologically. All are transmitted by the bite of the tse tse fly (*Glossina palpalis*). Typically, an ulceration will appear in the area of the bite (trypanosomal chancre) that slowly disappears. Incubation periods range from days to weeks during which time the patient is symptomless although trypanosomes can be found in the blood. Infections can be abortive or invade the lymphatic tissues which is signaled by the onset of rigor and febrile attacks lasting for weeks or even months. Malaise and headache usually accompany an attack along with night sweats and an overall anorexia. Often nodes become visible (Winterbottom's sign) and there is an increasing lassitude and apathy in the patient as the disease progresses to central nervous system (CNS) involvement. As mental faculties deteriorate, there is a general fatigue, confusion and somnolence. Extreme emaciation is observed in patients who have received little or no medical attention. Motor function becomes increasingly difficult with an evident slurring of speech and an ataxic gait. Pressure on the palms produces severe pain after the pressure is removed (Kerandel's sign), a signature characteristic of the disease.

In the final stages, there are profound character changes and mental deterioration accompanied with convulsions, hemiplegia and paraplegia, incontinence and severe paresthesia until the patient becomes comatose. Relapses and remissions are common and can continue for years until the patient eventually succumbs. Treatment is typically melarsoprol, Mel B or melarsen oixide complexed with dimercaprol. Suramin is generally effective, but additional drugs which can be used include pentamide and derivatives of melarsoprol.

American trypanosomiasis (Chagas disease) is caused by *Trypanosoma cruzi* and occurs throughout the southern parts of North America and northern parts of South American. These parasites are transmitted from the bite of the reduviid bug (*Panstrongylus megistus*). The disease is sever in children under five where central nervous system involvement predominates. The site of the infection occurs most frequently on the face creating an intense inflammatory reaction or a chagoma (Roman's sign). Symptoms appear in about four to fourteen days after the bite. Promastigotes migrate to the lymph system and quickly lodge to regional lymph nodes where they are ingested by cells in the node. Within these cells, promastigotes transform into amastigotes which can migrate throughout the body and lodge within the tissues of any organ.

In adults there are few symptoms, but in children there can be chills, high fevers, muscular aches, an increasing exhaustion and epitaxis. Liver, spleen and cardiac cells tend to be favorite sites of infection. Chronic infections are accompanied by heart problems such as massive cardiomegaly and fibrosis. The only effective treatment is nitrofurfurylidine derivative Bayer 2502 (Nifurtimox). It is most useful in early stage and acute stages of the disease and requires extended treatment periods.

Another major hemoflagellate disease is leishmania which can be produced from a variety of species of Leishmania, all of which are transmitted by the sandfly (Phlebotomus). Cutaneous leishmaniasis, the oriental sore, is caused by *Leishmania tropica* found throughout Asia Europe and Africa, and *L. mexicana* which is endemic to the Americas. Incubation periods after an initial infection may require months or even years. During incubation there are few, if any, symptoms. Small red papule may appear on the skin at the site of infection which will itch and form open ulcerations with a serious exudate. Most lesions heal spontaneously as a natural immunity develops. Exposure confers absolute resistance to reinfection by the same species.

Mucocutaneous leishmardasis (*L. braziliensis*) and visceral leishmaniasis or kala-azar (*L. donovani*), are transmitted by sandflys. As their names implies, these diseases affect specific tissues of the patient. Symptoms include ulcerations of the soft tissues and in the more serious cases, complete destruction and loss of cartilaginous tissues. Visceral leishmaniasis can occur at any area of the body and is generally preceded by a darkening at the site of infection and a parasitemia of the reticuloendothelial system throughout the body. Mucocutaneous leishmaniasis is more restricted to the mucosal tissues where secondary infections become common and prominent.

Treatment for all forms of leishmaniasis requires administration of sodium gluconate (Pentostam) which is considerably less toxic than most antimoniuals. Side-effects with these drugs are common.

One of the most well-known parasitimias in the world today is malaria. Malaria can present itself as several different clinical syndromes which are now known to be caused by several different species of Plasmodium including *P. falciparum, P. vivax, P. ovale* and *P. malariae*. Both morphologically and clinically, each can be easily distinguished (Table 1).

TABLE 1

Comparison of the Clinical Course of Various Forms of Plasmodium.

| | P. vivax | P. ovale | P. malariae | P. falciparum |
|---|---|---|---|---|
| Incubation Time (days) | 10–17 | 10–17 | 18–40 | 8–11 |
| Severity | severe | mild | severe | mild |
| Fever pattern | irregular quotidian | irregular quotidian | regular 72 hours | continuous quotidian |
| Periodicity (hours) | 48 | 48 | 72 | 36–48 |
| Untreated Duration | 5–7 years | 12 months | 20+ years | 6–17 months |
| Anemia | ++ | + | ++ | ++++ |
| CNS Involvement | + | +/− | + | ++++ |
| Nephrotic Syndrome | +/− | − | +++ | + |

Human malaria was first recognized in the late 1800's and by the early 1900's, the entire life cycle of the parasite from man to mosquito was known. During this period, it was also discovered that Plasmodium occurs in others species of mammals as well as man. The life cycle of the parasite begins when the female mosquito bites an infected person and ingests infected blood containing male and female gametocytes. In the mosquito, the male gametocyte undergoes a process of maturation, termed exflagellation, extruding delicate spindle-shaped gametes. Simultaneously, the female gametes also mature and become fertilized by the male gametes forming zygotes. These zygotes elongate into ookinetes which penetrate the stomach wall of the mosquito lodging within the outer covering of cells to become oocysts. The oocyst develops into thread-like sporozoites that break out and wander throughout the mosquito's body, eventually finding their way into the salivary glands to be introduced into the blood stream of the mosquito's next host.

Once injected the sporozoites leave the blood vascular system within about forty minutes and invade the parenchymal cells of the liver. In the liver, the parasites undergo a period of asexual development termed the pre-erythrocytic stage. After maturation, parasites are liberated into the blood stream to infect red blood cells. Another stage of asexual development occurs in red blood cells in a process termed schizogony. Within a period of about 72 hours, handfuls of new parasites form from each infected cell. Details of this cycle differ from species to species. At the end of this period, red blood cells rupture liberating more merozoites which in turn infect more cells. It has been suggested that fever induced by the near simultaneous rupture of large numbers of red blood cells dumping large amounts of toxins into the blood stream has some regulatory effect on the developmental cycle. Febrile periodicity becomes synchronized at 48–72 hour intervals depending on the species.

At some time after asexual development, gametocytes appear in red blood cells and the patient begins to show pathologic signs of infection. These parasitic forms continue to grow and develop asexually, but do not divide and eventually form the male and female forms. It is these forms which are ingested by the mosquito to begin the cycle again.

Treatment regiments for malaria are quite varied. Colchicine, sulfones such as diaminodiphenylsulfone (dapsone), and the longer-acting sulfonaminides are PABA antagonists interfering with the synthesis of folic acid from para-aminobenzoic acid which effects the schizont stage of the erythrocytic life cycle. Chlorguanide (Paludrine), a biguanide, and the structurally related drugs diaminopyrimidine and pyrimethamine (Daraprim), are relatively slow-acting anti-malarials that effect the sexual erythrocytic stages of malaria by interfering with the metabolism of folic acid.

The three separate stages of the plasmodial life cycle in man cannot be successfully treated with any single drug. The pre-erythrocytic and erythrocytic cycles are sensitive to primaquine and also to chlorguanide and pyrimethamine. The sexual stages respond to quinine, chloroquine, hydroxychloroquine, amodiaquine and quinacrine, chloroquine and pyrimethamine, sulfonamides and sulfones, and colchicine. Combination therapies are designed based on these various modes of action. Chemoprophylaxis is usually performed for those who must travel into endemic areas and for those uninfected individuals who may require extra measures of protection. The drugs of choice for prophylaxis are chloroquine and hydroxychloroquine. All of these drugs have been used extensively in areas of the world in which malaria is endemic. Unfortunately, significant resistance has also developed in the various species as well.

Others parasitemias of man include the trematodes such as the liver flukes (*Fasciola hepatica*, Opisthorchis and Dicrocoelium), the intestinal flukes (*Fasciolopsis buski*, the Echinostomes and the Heterophyids), and the liver flukes (*Paragonimus westermani* and *P. heterotremus*). These organism are extremely varied with complex life cycles. Lung flukes are treated with bithionol which is widely used in medicated shampoos and soaps. Intestinal flukes are treated with niclosamide (Yomesan) which can be absorbed through the gastrointestinal tract. Praziquantel is the treatment of choice for liver flukes.

The blood flukes, *Schistosoma mansoni*, *S. japonicum* and *S. haematobium*, are of particular importance because of their widespread distribution. These parasites cause a very large portion of morbidity and mortality in the world today. Schistosomes have a complex life cycle which generally begins in eggs that find their way into bodies of water from contaminated feces. Once in contact with water the eggs hatch into miracidium which infect the snail. Within the snail, larval stages develop giving rise to large numbers of cercariae that are subsequently liberated into the water. Humans infection occurs upon contact with cercariae infested water as the parasites penetrate directly through the skin. After penetration, parasites invade blood vessels and are carried to the lungs and than the liver where they begin their growth. About two weeks later, adult worms begin a migration against the flow of blood and into the portal system lodging in the mesenteric or vascular veins. Final locations differ for each species. Eggs are produced which travel throughout the body. Some travel to the intestines to be excreted to begin the cycle again while others lodge in various parts of the body.

Upon penetration of the skin there is sometimes a transient reaction such as edema and puritis, but little more. During incubation there may be allergic reactions and a generalized malaise or fever. When the flukes reach their final location, the acute stage of the disease begins and symptoms vary from mild to severe. There is usually some intestinal and bladder pain and tenderness, diarrhea, fever, dysuria and hematuria accompanied by eosinophilia. In the third stage the disease become chronic and many of the complications associated with third stage schistosomiasis can be attributed to the eggs. There is extensive fibrosis and hyperplasia of the tissues where eggs are deposited. Abscesses form with severe hepatomegaly and splenomegaly. In addition, the loss of red blood cells is severe. Adult females have been demonstrated to consume as many as 300,000 red blood cells per hour and adult males about 30,000. In areas where individuals are likely to be infected, nutrition is already quite poor complicating treatment and any good prognosis for recovery.

Blood flukes are treated with potassium antimony tartrate or tartar emetic, a trivalent antimony compound which for a long time was the treatment of choice. Stibophen and oxamniquine are used and have demonstrated some effectiveness. Antimonials are contra-indicated in the presence of cardiac or renal disease. Oxamniquin (Vansil) is the drug of choice with *S. mansoni* and metrifonate (Bilarcil) for *S. haematobium*. Niridazole (Ambilhar) is acceptable for most infections and is typically effective against *S. japonicum*. Other compounds which may be useful include amoscanate, praziquantel and sodium antimony dimercaptosuccinate (Astiban).

Although there has been some success with current treatments of parasitic infections, these diseases remain serious sources of morbidity and mortality in the world.

SUMMARY OF THE INVENTION

The present invention overcomes the problems and disadvantages associated with current strategies and designs and provides new methods for the treatment and prevention of diseases and disorders related to infection by eukaryotic organisms.

One embodiment of the invention is directed to compositions containing an adenosine derivative and, optionally, a deaminase inhibitor. Examples of useful adenosine derivatives include cordycepins, cordycepin analogs and derivatives, and modifications of these molecular structures. Examples of useful deaminase inhibitors include coformycins, coformycin analogs and derivatives and modifications thereof. Preferably, the adenosine derivative is in an excess over the deaminase inhibitor. These compositions can be used in vivo for the treatment of mammals or in vitro for the treatment of biological products.

Another embodiment of the invention is directed to methods for the treatment of patients suspected of being infected with a parasitic organism comprising the administration to the patient an adenosine derivative and, optionally, a deaminase inhibitor. Treatments may be administered parenterally, sublingually, enterally, by pulmonary absorption or by topical application, but are preferably intravenous or intraperitoneal. Adenosine may be administered simultaneously with or shortly before or after the deaminase inhibitor. Patients which may be successfully treated include most mammals such as humans, dogs, cats, camels, cattle, sheep, pigs, goats and rodents. These methods can result in complete elimination of parasitemia from the patient and resolution of all symptoms associated with infection.

Another embodiment of the invention is directed to methods for the prevention of infections by parasitic organisms. A patient at risk of being infected with a parasite is administered an adenosine derivative and, optionally, a deaminase inhibitor. The patient maintains both components in their system to destroy or inactivate any organisms before an infection can be initiated.

Another embodiment of the invention is directed to methods for the treatment of biological products such as living cells or tissues to prevent or eliminate a parasitic contamination. Treatments can be applied to whole blood, fractionated blood, plasma, serum, and transplantable organs, and involve incubation of the biological product with an adenosine derivative and, optionally, a deaminase inhibitor for a predetermined period of time.

Another embodiment of the invention is directed to methods for the treatment of biological products such as materials derived from living cells or tissues, or foods to prevent or eliminate a parasitic contamination. Treatments can be applied to products purified from cells such as cytokines, immune system regulators, recombinant proteins and blood products. Treatments involve incubation of the biological product with an adenosine derivative and, optionally, a deaminase inhibitor.

Other embodiments and advantages of the invention are set forth, in part, in the description which follows and, also in part, will be obvious from this description or may be learned from the practice of the invention.

DESCRIPTION OF THE INVENTION

As embodied and broadly described herein, the present invention is directed to compositions and methods for the treatment and prevention of parasitic infections of and by eukaryotic organisms.

One embodiment of the invention is directed to pharmaceutical compositions useful for the prevention and treatment of parasitic infections by eukaryotic organisms. Compositions contain an adenosine derivative comprising a five-membered pentose ring coupled to a purine. Preferably, the adenosine derivative has the formula:

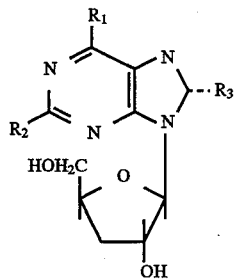

wherein $R_1$, $R_2$ and $R_3$ are each a chemical moiety such as hydrogen, hydroxyl, halide, alkyl or alkoxyl, amine or amide, sulfhydral, phosphoryl sulfinyl or sulfonyl, or a combination or derivative of these chemical moieties. Additionally, $R_1$, $R_2$ and $R_3$ and may be the same or different. More preferably, $R_1$ is OH, SH, $SCH_3$ or $NHCH_3$; $R_2$ is H, F, Cl, Br, I or $NH_2$; and $R_3$ is H, F, Cl, Br, I or $CH_3$. Examples of useful adenosine derivatives include cordycepin (3'-deoxyadenosine) and cordycepin derivatives. Derivatives may be identified from existing compounds by testing as herein described or as known in the art. Derivatives may also be organically or enzymatically created with techniques such as, for example, rational drug design and empirical screening using the disclosures provided herein and the knowledge of one of ordinary skill in the art.

Compositions of the invention are effective against a wide variety of parasites. Many of these are transmitted by insects and an essential stage of the life cycle may take place in the insect host or be transmitted to man from another animal host by an insect. Examples of parasitic diseases which can be treated by compositions of the invention include those which infect the blood, the tissues, the lymphatic system, major organs and organ systems, the dermis and the gastrointestinal tract. Examples include species of the genera Entamoeba, Ascaris, Ancyclostoma, Strongyloides, Trichuris, Wuchereria, Leishmania, Plasmodium, Toxoplasma, Sarcocystis, Pneumocystis, Schistosoma, Loa, Onchocerca, Brugia, Dipetalonema, Mansonella, Dracunculus, Babesia and Trypanosoma.

The mechanism of action of an adenosine derivative of the invention is directed to the disruption of enzymatic processes of the parasite that relate to the metabolism of purine, purine derivatives and purine-like chemical structures. These processes are basic reactions that exist in all organisms. Purines and related compounds are involved in biosynthetic and enzymatic pathways such as nucleotide biosynthesis including the synthesis of ATP and GTP, nucleic acid and protein biosynthesis, intracellular and extracellular cellular signaling, mitosis, meiosis, DNA replication, RNA transcription, folate metabolism, the activities of protein kinases A and C, the purine cycle, excretion, absorption and secretion, and other processes considered fundamental to life. Parasites are acutely sensitive to interference of these processes, and thus, compositions that specifically target these reactions can be used to selectively eliminate an infection or ameliorate the pathogenic symptoms associated with a parasitic infection by reducing parasitemia without unnecessary injury to the host.

Compositions of the invention contain an adenosine derivative at a concentration of between about 1.0 mM to about 10 mM. Such compositions may be concentrated forms of the active ingredients or may be unconcentrated and suitable for immediate use. Alternatively, compositions which are liquids (vol./vol.) or solids (wt./wt.), may contain active components at between about 0.001% to about 100%, preferably between about 0.01% to about 10.0%, and more preferably between about 0.1% to about 5.0%, but may be further diluted, if necessary, such as for prolonged direct contact with skin or other bodily tissues where such contact would be harmful to the patient. Compositions may also contain a pharmaceutically acceptable carrier to facilitate administration or introduction to a patient or biological product, to maintain or increase physiological stability, or to facilitate storage or half-life of the composition. Useful pharmaceutically acceptable carriers include water, various oils, salts, saccharides and polysaccharides, glycerols, collagens and combinations and modifications of these substances. Compositions of the invention may optionally include flavoring agents and other agents that may be necessary or desirable to increase shelf-life, such as preservatives, anti-oxidants and other components advantageous for manufacture and distribution of the composition.

Compositions of the invention may optionally contain a deaminase inhibitor such as the adenosine deaminase inhibitor coformycin and derivatives of coformycin such as deoxycoformycin. Certain adenosine derivatives are enzymatically deaminated into inactive inosine by deaminases which may be present in the patient or the article being treated. The addition of such an inhibitor prevents deamination of the adenosine derivative, and thus, its inactivation. Further, deaminase inhibitors have an effective role in treatment. For example, deaminase inhibitors diminish the metabolism of deoxyadenosine to deoxyadenosine triphosphate and alter the activity of certain kinases and polymerases. These activities may also have a useful effect against the parasite. Deaminase inhibitors such as coformycin and deoxycoformycin are safe and non-cytotoxic at useful concentrations. Compositions of the invention which include a deaminase inhibitor contain this component at a concentration of between about 0.1 nM to about 1.0 mM. Alternatively, compositions which are liquids (vol./vol.) or solids (wt./wt.) may contain between about 0.001% to about 100%, preferably between about 0.01% to about 10.0%, and more preferably between about 0.1% to about 5.0% of the deaminase inhibitor, but may, if necessary, be further diluted.

Compositions of the invention containing both an adenosine derivative and a deaminase inhibitor will preferably have an excess of the adenosine derivative over the inhibitor. The adenosine derivative will preferably be in a two- to twenty-fold excess over the deaminase inhibitor and more preferably in a five- to ten-fold excess. The deaminase inhibitor may be administered prior to, subsequent to, or simultaneous with the adenosine derivative. The composition may contain these two ingredients in a mixture to be administered together or the two may be kept separate and administered separately. As both adenosine derivatives and deaminase inhibitors can be effectively dissolved in aqueous solutions, they can be easily utilized as mixtures in liquid or solid form.

Another embodiment of the invention is directed to compositions wherein the adenosine derivative is coupled to the deaminase inhibitor. Coupling may be by ionic bonding such as hydrogen bonding, covalent bonding and affinity bonding. Preferably, the bond formed is stable when used in vivo or in vitro. In compositions where the adenosine derivative and the deaminase inhibitor are separate, it may be difficult to effectively administer both components. Compositions wherein the two components are coupled together are effective for treating or preventing an infection because the deaminase inhibitor is effective in all locations where the adenosine derivative is active. Compositions can be used in vivo to treat human patients infected or suspected of being infected with a parasitic organism, or in vitro to treat a biological product suspected of being contaminated with a parasite.

Another embodiment of the invention is directed to a method for treating a patient suspected to be at risk of or at risk of being infected with a parasite. Diseases which can be treated include parasitic infections of the blood, lymph and tissues such as trypanosomiasis, leishmania, toxoplasmosis, sarcocystis, pneumocystis, schistosomiasis and elephantitis. Organisms responsible for these diseases include species of the genera Leishmania, Plasmodium, Toxoplasma, Sarcocystis, Pneumocystis, Schistosoma, Wuchereria, Loa, Onchocerca, Brugia, Dipetalonema, Mansonella, Dracunculus, Babesia and Trypanosoma.

The patient being treated is administered a therapeutically effective mount of a composition of the invention. Patients which can be treated include mammals such as a dog, cat, horse, cow, cattle, pig, sheep, goat, rodents, camels or chicken, or a wild animal, but is preferably a human. Zoo animals such as monkeys (primates) also tend to acquire parasitic infections which are treatable with compositions of the invention. Passage through a non-human host is often a requisite part of the life cycle of a parasite. Elimination of the parasite in the animal host is an effective means for eliminating or preventing infections in humans. As compositions of the invention are non-toxic at effective concentrations, compositions can safely be used to treat both human and non-human patients.

Administration may be to an adult, an adolescent, a child, a neonate or an infant, or even to a patient in utero. Dosages range from between about 1 ng/kg patient weight to about 10 mg/kg patient weight. Administration of the composition may be for a short term, continuous or sporadic as necessary. Patients with a suspected or diagnosed parasitic infections may only require treatments for short periods of time or until the infection has proceeded to remission or has been effectively eliminated. Alternatively, to effectively eliminate certain parasites, administration may require long term treatments such as for months or years. As compositions of the invention are generally safe and non-toxic at required dosages, this does not present a problem.

Compositions are administered in a manner which is most useful for the infection being treated. Useful methods of administration include oral, parenteral, sublingual, rectal or enteral administration, pulmonary absorption or topical application. Parenteral administration may be by intravenous injection, subcutaneous injection, intramuscular injection, intra-arterial injection, intrathecal injection, intraperitoneal injection or direct injection or other administration directly to the site or sites of infection. Injectable forms of administration are sometimes preferred for maximal systemic effect. When long term administration by injection is necessary medi-ports, in-dwelling catheters, or automatic pumping mechanisms may be used. These devices provide direct and immediate access to the arteries in and around the heart and other major organs and organ systems. Such devices are useful for treating parasitic diseases that infect organs and organ systems such as the blood and tissue dwelling nematodes, malaria, trypanosomiasis and leishmania.

Another effective method of administering compositions to infectious sites may be by transdermal transfusion such as with a transdermal patch and other means of direct contact with affected tissues, or by administration to an internal infection through an incision or some other natural or artificial opening into the body. Compositions may also be administered to the nasal passages as a spray. Diseases localized to the respiratory tract, the head and brain area are treatable in this fashion as arteries of the nasal area provide a rapid and efficient access to the upper areas of the body. Sprays also provide immediate access to the pulmonary system and the bloodstream. Nasal sprays are a preferable method for administering compositions to these areas and useful to treat diseases caused by species of the genera Trypanosoma, Leishmania, Plasmodium and Schistosoma. Access to the gastrointestinal tract is also achievable using oral, enema, or injectable forms of administration. Such forms of compositions may also be useful to treat gastrointestinal disorders such as Entamoeba, the flagellates *Giardia lamblia, Dientamoeba fragilis* and *Trichomonas vaginalis*, the nematodes Ancyclostoma, Ascaris, Enterobius and both cutaneous and visceral leishmaniasis. Compositions may be administered as a bolus injection or spray, or administered sequentially over time (episodically) such as every two, four, six or eight hours, every day (QD) or every other day (QOD), or over longer periods of time such as weeks to months for as long as it takes the infection to resolve or for the patient's own system to be able to overcome the infection.

Orally active compositions are preferred as oral administration is usually the safest, most convenient and economical mode of drug delivery. Oral administration may often be the most effective method to administer compositions directed to parasites of the gastrointestinal tract such as infections by *Entamoeba histolytica*, *E. coli*, *E. poleki*, *Ascaris lumbricoides*, *Giardia lamblia*, *Enterobius vermicularis*, *Necator americanus*, *Wuchereria bancrofti* and various species of Ancyclostoma. Oral administration can be disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity without significantly compromising their functional activity. This can often be accomplished by formulating a composition with a complimentary reagent which neutralizes its polarity, or modifying the compound with a neutralizing chemical group. Oral bioavailability is also a problem because drugs are exposed to the extremes of gastric pH and gastric enzymes. These problems can be overcome in a similar manner by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

When the composition is administered orally, it may be in the form of a liquid, a spray, a powder, a pill, a tablet or a capsule. To facilitate oral administration, compositions of the invention will preferably include flavoring agents and other agents to increase shelf-life.

Administration by any method can be accurately quantitated by measuring levels of the composition from a sample of bodily fluid such as blood, serum or plasma. Effective serum levels of active components of the invention such as the adenosine derivative or deaminase inhibitor are between about 0.01 nM to about 1.0 mM, preferably between about 1.0 nM to about 0.1 mM, and more preferably between about 10.0 nM to about 50.0 mM. Effective levels of the deaminase inhibitor may be between two- and twenty-times lower than effective levels of the adenosine derivative. When applied by direct contact, effective levels of active ingredient may sometimes be analyzed by determining concentration of the composition in the areas which are in close contact with the area of application. For example, when applied topically to the skin, effective levels may be determined from fluid or tissue samples of the dermal tissues within a few centimeters under the area of application. In such cases, composition strength may be predetermined and used as a concentrated solution.

Compositions can be administered by oral or enema formulations, or by rectal irrigation to maximize their contact with and effectiveness on the gastrointestinal system. In such cases, dosages are between about 1% to about 20% (vol/vol.) or between about 1 mM to about 100 mM. Doses are administered until symptoms improve sufficiently for the patient's immune system to resolve the infection or the parasite is killed or eliminated. Multiple and frequent dosing is not problematic because the compounds of the invention are safe, non-toxic and physiologically stable.

Positive effects of treatment include a reduction of parasite load or parasitemia, death or inactivation of the parasite, decreased infectivity of the parasite, or elimination of the parasite from the body. Preferably, the patient has a parasitemia which is reduced at least 100-fold, more preferably 1000-fold, and even more preferably is undetectable after treatment. Parasitemia may be determined by growing parasites from biological samples obtained from the patient suspected to be infected with the parasite into suitable cultures and counting the parasites which can be grown.

Alternatively, biological samples are obtained from selected ares of the patient suspected to be infected and the numbers of parasites visualized directly or indirectly under a microscope or other suitable devise and counted. Fluorescent-conjugated antibodies may also be used in, for example, an ELISA or other markers to detect parasitic antigen or anti-antigen antibodies in a biological sample to determine the degree of infection and the effect of treatments.

Another embodiment of the invention is directed to compositions of the invention which can be used in combination with other agents to maximize the effect of the compositions in an additive or synergistic manner. Agents which may be effective in combination with the compositions of the invention include other drugs and treatments which are known or suspected to have a positive effect against the parasite. Examples of additional agents known to be effective against one or more pathogenic parasites include benznidazoles, nitrofurfurylidines, dimercaprols, suramins, pentamidines, melarsoprols, melarsen oxides, quinines, sulfonamides, sulfones, chloroquines, pyrimethamines, antimony sodium gluconates, sulfadiazines, and derivatives, modifications and combinations of these agents. Therapies using various combinations of these agents would be safe and effective therapies against infections. Combinations of therapies may also be effective in inducing suppression or elimination of an infection such as compositions of the invention plus radiation therapy, toxin or drug conjugated antibody therapy using monoclonal or polyclonal antibodies directed against, for example, the parasite, infected cells, gene therapy or specific anti-sense therapy. Effects may be additive, logarithmic, or synergistic, and methods involving combinations of therapies may be simultaneous protocols, intermittent protocols or protocols which are empirically determined.

Another embodiment of the invention is directed to compositions described above which can be used prophylactically. For example, patients exposed to areas where a parasitic disease is endemic may be continuously treated with compositions to prevent a parasitic infection from taking hold. Patients who have been genetically screened and determined to be at high risk for the future development of an infection may also be administered compositions, possibly beginning at birth and possibly for life. Administration may be by any means described and dosages may be reduced in comparison to dosages required for treatment. Both prophylactic and therapeutic uses are readily acceptable because these compounds are generally safe and non-toxic at useful dosages.

Another embodiment of the invention is directed to methods for the treatment of biological products suspected of being contaminated with a parasite. Products which can be treated or pretreated include whole blood, fractionated blood, plasma, serum, transplantable organs, living cells including bone marrow, stem cells, primary cells surgically obtained and established cell lines, and products derived from living cells. Products which can be derived from living cells include blood products such as insulin, the blood clotting factors (e.g. Factor V, VIII, VIII, IX, X, XI, XII), cytokines (e.g. interferon α, β or γ; the interleukins Il-1, Il-2, Il-3, etc.), complement proteins, antibodies, immune system regulators, recombinant proteins and other macromolecular products.

Treatment involves contact of the biological product with a solution comprising an adenosine derivative and, optionally, a deaminase inhibitor. Products may be sprayed, powdered, sprinkled, misted, subjected to pressurizing conditions, submerged, coated or otherwise administered compositions of the invention to foster contact between the composition and the parasite. Contact may also be encouraged by incubating compositions of the invention with the product. Incubations may be performed at between about 0° C. to about 50° C., preferably between about 4° C. and about 37° C., and more preferably at about room temperature (18°–22° C.). For example, the biological product, which may be living, is placed in a sterile container and sprayed or immersed in a solution or spied with a powder containing an adenosine derivative and a deaminase inhibitor at an effective concentration. The deaminase inhibitor may not be necessary, for example, where there are no deaminases to inactivate. The product is maintained in this solution for a period of time necessary to effectively inactivate or destroy the parasite. This time period may be minutes to weeks, but is preferably between about one minute to one week, more preferably between about one hour to one day. The product is than removed from the solution, washed if necessary, and utilized as desired. As compositions of the invention are generally safe and non-toxic, removal of product may not even be necessary, washing may not be necessary and the product may even be stored or shipped in the composition. In such cases, compositions of the invention may also contain additional components useful or desirable to accommodate the product during storage or shipping.

For example, biological products such as blood and blood products are required in vast quantities world-wide including areas of the world where parasitic diseases are endemic. Food and food products (salts and spices, sugar, molasses, sorghum, alimentary paste, dairy products, oils) including grains and vegetables (corn, wheat, rice, barley, peas, soybeans), breads, fruits (grapes, citrus fruits, bananas, apples, pears) and even fish and meats can be similarly treated. Maintaining an effective quantity of an adenosine derivative and, optionally, an effective quantity of a deaminase inhibitor in such supplies may prevent the spread of parasitic diseases from such products. Other products which are also required for medical uses include bone marrow and transplantable organs. Such products are typically obtained locally under emergency conditions. In such cases, there may be an undetected parasitic infection that would be passed to the patient receiving the product. Prophylactic treatment of these products would alleviate this risk and, as compositions of the invention are effective against a broad range of parasites, treatment only requires contact with this one composition. Multiple treatments would not be required or could be significantly reduced, increasing the overall chances of success for the therapy being administered to the patient.

The following examples illustrate embodiments of the invention, but should not be viewed as limiting the scope of the invention.

EXAMPLES

Example 1

Parasitemia and Mortality in Therapeutically Treated *Trypanosoma brucei* Infected Mice.

Balb/c mice were injected (i.p.) with approximately $5 \times 10^5$ *Trypanosoma brucei* (an TaT 1/1 rodent adapted strain) organisms obtained from the peripheral blood of appropriately infected mice for all experiments. Equal numbers of organisms were injected into 6 or 7 mice on day 0, day 2 and day 3. The therapeutic effect of 3'-deoxyadenosine (cordycepin) along with the adenosine analogs fludarabin monophosphate, leustatin (2-Cl-2'-deoxyadenosine), 2-Cl-3'-deoxyadenosine, 2-F-3'-deoxyadenosine, which are not deaminated by adenosine deaminase (all obtained from Sigma Chemical; St. Louis, Mo.), were tested. Coformycin and deoxycoformycin were used as inhibitors of the adenosine deaminase. All reagents were diluted in phosphate buffered saline (PBS), fractionated and stored at −20° C. until use.

Mice were infected with *T. brucei* parasites and treated with 10 μM cordycepin plus 1 μM coformycin daily for five days. Parasites were scored four days after infection. No parasites were found in the treated groups whereas there were an average of $16.9(\pm 4.8) \times 10^6$ parasites per ml in the non-treated group.

Mice were again injected daily starting on day 2 after infection with an adenosine derivative either alone or in combination with coformycin, or remained untreated as controls. Concentrations of 5 μM and 10 μM were chosen as tests at 30 μM were toxic to the mice. At these lower concentration, no toxic effects (wasting, diarrhea) were observed. Results are shown in Table 2.

TABLE 2

| Treatment | Parasitemia Post Infection* | | Cumulative Mortality | |
|---|---|---|---|---|
| | 4 Days | 7 Days | 8 Days | 10 Days |
| Control | 61 ± 13 | 36400 ± 6900 | 5/6 | 6/6 |
| Cordycepin (5 μM) | 0 | 2500 ± 1100 | 0/6 | 1/6 |
| Cordycepin (10 μM) | 0 | 1700 ± 700 | 1/6 | 2/6 |
| 2-Cl-3'-dA | 146 ± 54 | nd | 3/6 | 6/6 |
| 2-F-3'-dA | 44 ± 22 | nd | 2/6 | 6/6 |
| Fludarabin monophos. | 2.1 ± 6 | 8233 ± 3900 | 1/6 | 6/6 |
| Leustatin | 216 ± 60 | nd | 5/6 | 6/6 |
| Cordycepin (10 μM) + Coformycin (1 μM) | 0 | 0 | 0/6 | 0/6 |

*= Paraitemia ± SEM × $10^{-4}$/ml.

Parasitemia was measured periodically and mortality recorded. The Mann-Whitney-Wilcoxon U test was used to compare parasitemia levels and mortality was analyzed by a chi-square test. Difference with the control group were significant (p=less than 0.002) in tests using cordycepin, fludarabin monophosphate, 2-Cl-3'-dA and cordycepin plus coformycin.

As shown, daily administration of 10 μM cordycepin +1 μM coformycin cured infection of *T. brucei* as measured by the complete absence of parasites and mortality (Table 2). The mean parasitemia of control mice was $5-20 \times 10^6$ trypomastigotes per ml at day 4 after infection and all died by day 7–9 after infection. Mice injected daily with 10 μM cordycepin also controlled the infection with *T. brucei*. When mice were treated with 1 μM coformycin alone, there was no difference observed in parasitemia or mortality as compared to controls (see Table 3).

Although cordycepin proved more effective, treatment with the deoxyadenosine analog fludarabin monophosphate, but not leustatin (2-Cl-2'-deoxy-adenosine), 2-Cl-3'-deoxyadenosine or 2-F-3'-deoxyadenosine at day 0 after infection with *T. brucei* diminished parasite levels as compared to controls and somewhat retarded mortality (Table 2). Fludarabin monophosphate and coformycin were not able to clear *T. brucei* infections.

Similar tests were performed in additional experiments using dosages of cordycepin and coformycin. Parasitemia was measured periodically and mortality recorded. The Mann-Whitney-Wilcoxon U test was used to compare parasitemia levels and mortality was analyzed by a chi-square test. Results that were achieved are tabulated in Table 3.

TABLE 3

| Treatment | Parasitemia Post Infection* 4 Days | Cumulative Mortality 7 Days |
|---|---|---|
| Control | 4170 ± 1690 | 6/6 |
| Cordycepin (10 μM) | 1013 ± 285 | 6/6 |
| Cordycepin (10 μM) + Deoxycoformycin (2.5 μM) | 0 | 0/6 |
| Cordycepin (10 μM) + Coformycin (1.0 μM) | 0 | 0/6 |

*= Parasitemia ± SEM × $10^{-4}$/ml.

Difference with the control group were significant in all cases (p=less than 0.01). All mice survived and cleared the parasite load when 10 μM cordycepin and 1 μM coformycin were injected at days 2 and 3 after infection. Administration of 2.5 μM deoxycoformycin and 10 μM cordycepin at days 2 and 3 after infection also resulted in clearance of T. brucei parasites (Table 3). Daily administration of 5 μM or 10 μM cordycepin starting from day 2 to day 5 after infection did not cure T. brucei infected mice, although a therapeutic effect was observed.

Example 2

Parasitemia and Mortality in Prophylactically Treated Trypanosoma brucei Infected Mice.

Compositions were also tested prophylactically for effect against parasitemia in T. brucei infected mice treated prophylactically.

TABLE 4

| Treatment | Parasitemia Post Infection* 4 Days | Cumulative Mortality 7 Days |
|---|---|---|
| Control | 4141 ± 514 | 6/6 |
| Coformycin (1 μM) | 3810 ± 1365 | 6/6 |
| Cordycepin (10 μM) | 1000 | 6/6 |
| Cordycepin (1 μM) + Coformycin (10 μM) | 0 | 0/6 |
|  | 0 | 0/6 |

*= Parasitemia ± SEM × $10^{-4}$/ml.

Administration of 10 μM cordycepin plus 1 μM coformycin one hour before infection also protected mice from infection (Table 4). A single dose of 5 μM or 10 μM cordycepin was only partially protective. Mice showed a significantly reduced parasitemia and a delayed mean time of death as compared to controls.

Example 3

Parasitemia and Mortality in Trypanosoma cruzi Infected Mice.

Balb/c mice were injected i.p. with 2×$10^3$ Trypanosoma cruzi (Tulahuen strain) organisms obtained from the peripheral blood of appropriately infected mice for all experiments. Equal numbers of organisms were injected into 6 or 7 mice on day 0, day 2 and day 3. Mice were injected with 1 μM coformycin and/or 10 μM cordycepin once, at one-half hour before infection with T. cruzi organisms.

TABLE 5

| Treatment | Parasitemia Post Infection* | | Cumulative Mortality 21 Days |
|---|---|---|---|
|  | 10 Days | 14 Days |  |
| Control | 19 ± 2 | 159 ± 25 | 7/7 |
| Cordycepin (10 μM) + Coformycin (1 μM) | 8 ± 2 | 149 ± 9 | 2/6 |

*= Parasitemia ± SEM × $10^{-4}$/ml.

A lower parasitemia and time of death were evident between the group treated with both drugs and the controls (Table 5). All treated mice died within 30 days after infection. No differences in parasitemia were observed between mice receiving one injection of both drugs or mice receiving daily injections of cordycepin and coformycin with the control groups daily at the day of infection. Similar results were observed with therapeutic injections.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A method for the treatment of a patient infected with a trypanasonal parasite, comprising administering to said patient a therapeutically effective amount of a purine nucleoside and a deaminase inhibitor.

2. The method of claim 1 wherein the patient is a mammal.

3. The method of claim 1 wherein the mammal is selected from the group consisting of humans, dogs, cats, monkeys, cattle, sheep, horses, camels, pigs, goats and rodents.

4. The method of claim 1 wherein the purine nucleoside is administered parenterally, sublingually, enterally, by pulmonary absorption or by topical application.

5. The method of claim 4 wherein parenteral administration is by intravenous injection.

6. The method of claim 1 wherein the purine nucleoside is administered daily for multiple days.

7. The method of claim 1 wherein the therapeutically effective amount of the purine nucleoside is between about 1 ng/kg patient weight to about 10 mg/kg patient weight.

8. The method of claim 1 wherein treatment results in an purine nucleoside concentration in at least one measurable fluid of the patient of between about 0.1 nM to about 10.0 μM.

9. The method of claim 1 wherein the deaminase inhibitor is administered prior to the purine nucleoside.

10. The method of claim 1 wherein said deaminase inhibitor is administered together with said purine nucleoside.

11. The method of claim 1 wherein the therapeutically effective amount of the deaminase inhibitor is between about 1 ng/kg patient weight to about 10 mg/kg patient weight.

12. The method of claim 1 wherein treatment results in a deaminase inhibitor concentration in at least one measurable fluid of the patient of between about 0.1 nM to about 10.0 μM.

13. The method of claim 1 wherein the purine nucleoside is administered in a two to twenty fold excess to the deaminase inhibitor.

14. The method of claim 1 wherein the purine nucleoside is administered in a five to ten fold excess to the deaminase inhibitor.

15. The method of claim 1 wherein the purine nucleoside is a cordycepin.

16. The method of claim 1 wherein the purine nucleoside has the formula:

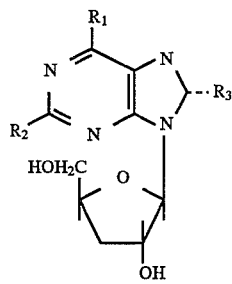

wherein $R_1$, $R_2$ and $R_3$ are each selected from the group consisting of hydrogen ions, hydroxyl ions, halides, alkyl and alkoxyl groups, amines and amides, sulfhydrals, nitryls, phosphoryls, sulfinyl and sulfonyl groups, and combinations thereof, and $R_1$ $R_2$ and $R_3$ may be the same or different.

17. The method of claim 16 wherein $R_1$ is —OH, —SH, —SCH$_3$ or —NHCH$_3$; $R_2$ is H, F, Cl, Br, I or NH$_2$; and $R_3$ is H, F, Cl, Br, I or CH$_3$.

18. The method of claim 1 wherein said deaminase inhibitor is a coformycin.

19. The method of claim 1 wherein said deaminase inhibitor is deoxycoformycin.

20. The method of claim 1 wherein the patient has a parasitemia which is reduced at least 100-fold after treatment.

21. The method of claim 1 wherein the patient has a parasitemia which is undetectable after treatment.

22. A method for the treatment of a biological product contaminated with a trypanasonal parasite comprised of contacting said biological product with an effective mount of a purine nucleoside and a deaminase inhibitor.

23. The method of claim 23 wherein the biological product comprises living cells.

24. The method of claim 23 wherein the living cells are selected from the group consisting of whole blood, fractionated blood, plasma, serum, bone marrow and transplantable organs.

25. The method of claim 22 wherein the biological product is a food product.

26. The method of claim 25 wherein the food product is selected from the group consisting of rice, wheat, barley, corn, soybeans, breads, oils, sugars, spices, dairy products, alimentary paste, vegetables and fruit.

27. The method of claims 22 wherein the biological product is derived from living cells.

28. The method of claim 27 wherein the biological product derived from living cells is selected from the group consisting of cytokines, antibodies, immune system regulators, recombinant proteins and blood products.

29. The method of claim 22 wherein the biological product is incubated in a solution comprising said purine nucleoside.

30. A method for the treatment of a patient infected with a plasmodium parasite, comprising administering to said patient a therapeutically effective amount of a purine nucleoside and a deaminase inhibitor.

31. The method of claim 30 wherein the patient is a human.

32. The method of claim 30 wherein the deaminase inhibitor is administered prior to the purine nucleoside.

33. The method of claim 30 wherein the deaminase inhibitor is administered together with the purine nucleoside.

34. The method of claim 30 wherein the purine nucleoside is administered in a two to twenty fold excess to the deaminase inhibitor.

35. The method of claim 30 wherein the purine nucleoside is administered in a five to ten fold excess to the deaminase inhibitor.

36. The method of claim 30 wherein the purine nucleoside is a cordycepin.

37. The method of claim 30 wherein the purine nucleoside has the formula:

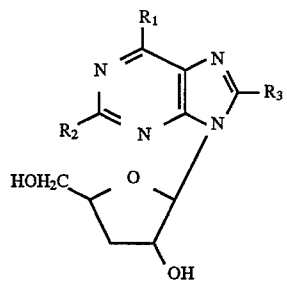

wherein $R_1$, $R_2$ and $R_3$ are each selected from the group consisting of hydrogen ions, hydroxyl ions, halides, alkyl and alkoxyl groups, amines and amides, sulfhydrals, nitryls, phosphoryls, sulfinyl and sulfonyl groups, and combinations thereof, and $R_1$ $R_2$ and $R_3$ may be the same or different.

38. The method of claim 37 wherein $R_1$ is —OH, —SH, —SCH$_3$ or —NHCH$_3$; $R_2$ is H, F, Cl, Br, I or NH$_2$; and $R_3$ is H, F, Cl, Br, I or CH$_3$.

39. The method of claim 30 wherein the deaminase inhibitor is a coformycin or a coformycin derivative.

40. The method of claim 30 wherein the deaminase inhibitor is deoxycoformycin.

41. The method of claim 30 wherein the patient has a parasitemia which is reduced at least 100-fold after treatment.

42. The method of claim 30 wherein the patient has a parasitemia which is undetectable after treatment.

43. A method for the treatment of a biological product contaminated with a plasmodium parasite comprised of contacting said biological product with an effective amount of a purine nucleoside and a deaminase inhibitor.

44. The method of claim 43 wherein the biological product comprises living cells.

45. The method of claim 44 wherein the living cells are selected from the group consisting of whole blood, fractionated blood, plasma, serum, bone marrow and transplantable organs.

46. The method of claim 43 wherein the biological product is a food product.

47. The method of claim 46 wherein the food product is selected from the group consisting of rice, wheat, barley, corn, soybeans, breads, oils, sugars, spices, dairy products, alimentary paste, vegetables and fruit.

48. The method of claims 43 wherein the biological product is derived from living cells.

49. The method of claim 48 wherein the biological product derived from living cells is selected from the group consisting of cytokines, antibodies, immune system regulators, recombinant proteins and blood products.

50. The method of claim 43 wherein the biological product is incubated in a solution comprising the purine nucleoside.

* * * * *